United States Patent
Maurer et al.

[11] Patent Number: 5,817,876
[45] Date of Patent: *Oct. 6, 1998

[54] PREPARATION OF N-ALKYL-ARYLAMINES

[75] Inventors: Fritz Maurer, Tochigi, Japan; Lothar Rohe, Wuppertal; Hans-Joachim Knops, Monheim, both of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 310,466

[22] Filed: Sep. 22, 1994

Related U.S. Application Data

[63] Continuation-in-part of Ser. No. 845,769, Mar. 2, 1992, abandoned, which is a continuation of Ser. No. 645,947, Jan. 25, 1991, abandoned.

[30] Foreign Application Priority Data

Feb. 2, 1990 [DE] Germany .......................... 40 03 078.4

[51] Int. Cl.⁶ .................................................. C07C 205/00
[52] U.S. Cl. ............................................ 564/397; 564/398
[58] Field of Search ...................................... 564/397, 398

[56] References Cited

U.S. PATENT DOCUMENTS

| | | |
|---|---|---|
| 3,261,869 | 7/1966 | Johnson . |
| 3,509,213 | 4/1970 | Greenfield . |
| 3,522,309 | 7/1970 | Kirby et al. . |
| 3,803,054 | 4/1974 | Kirby et al. . |
| 4,418,021 | 11/1983 | Patel . |
| 4,968,342 | 11/1990 | Foster et al. . |

FOREIGN PATENT DOCUMENTS

| | | |
|---|---|---|
| 929806 | 7/1955 | Germany . |
| 1014547 | 8/1957 | Germany . |
| 249279 | 9/1967 | Germany . |
| 2941070 | 4/1981 | Germany . |
| 9100262 | 1/1991 | WIPO . |

OTHER PUBLICATIONS

Dovell et al, "Platinum metal sulfides as heteregeneous hydrogenation catalysts", J. of Am.Chem/Soc. (1965), V. 20, pp. 2767–2768.

*Primary Examiner*—Alan Siegel
*Attorney, Agent, or Firm*—Sprung Kramer Schaefer & Briscoe

[57] ABSTRACT

Preparation of an N-alkyl-arylamine of the formula

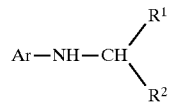

in which
Ar represents an aryl radical which is optionally monosubstituted or polysubstituted by at least one of halogen and in each case optionally substituted alkyl, alkoxy or alkoxycarbonyl,
$R^1$ represents hydrogen or alkyl and
$R^2$ represents in each case optionally substituted alkyl or aryl, or, together with $R^1$, represents alkanediyl,
by reacting a nitroarene of the formula $$Ar-NO_2 \qquad (II)$$

with a carbonyl compound of the formula $$R^1-CO-R^2 \qquad (III)$$

in the presence of hydrogen and in the presence of a catalyst at a temperature between 0° C. and 200° C.

9 Claims, No Drawings

PREPARATION OF N-ALKYL-ARYLAMINES

This application is a continuation-in-part of application Ser. No. 07/845,769 filed on Mar. 2, 1992, now abandoned which is a continuation of Ser. No. 07/645,947 filed Jan. 25, 1991 now abandoned.

The invention relates to an improved process for the preparation of N-alkyl-arylamines, which can be used as intermediates for agriculturally utilizable substances, in particular for herbicides.

It is known that N-alkyl-arylamines are obtained when arylamines are reacted either with alkyl halides (cf. J. Org. Chem. 24 (1959), p. 1551–1553) or with ketones in the presence of sodium borohydride and acetic acid (cf. J. Am. Chem. Soc. 96 (1974), p. 7812–7814; U.S. Pat. No. 4,418,021).

It is furthermore known in principle that N-alkyl-arylamines can be prepared from aromatic nitro compounds by reductive alkylation by means of catalytic hydrogenation in the presence of aliphatic ketones (cf. "Organic Reactions", Coll. Vol. 4, John Wiley and Sons, Inc., New York, 1948, p. 174 et seq., especially p. 188–189; J. Org. Chem. 29 (1964), p. 1265; U.S. Pat. No. 8,522,309).

However, the yield and/or quality of the products prepared in this manner are in many cases unsatisfactory.

It has now been found that N-alkyl-arylamines of the general formula (I)

in which
   Ar represents an aryl radical which is optionally mono-substituted or polysubstituted by halogen and/or by in each case optionally substituted alkyl, alkoxy and/or alkoxycarbonyl,
   $R^1$ represents hydrogen or alkyl and
   $R^2$ represents in each case optionally substituted alkyl or aryl, or, together with $R^1$, represents alkanediyl, are obtained in very good yields and in high purity when, in a "one-pot process", nitroarenes of the general formula (II)

in which
   Ar has the abovementioned meaning, are reacted with carbonyl compounds of the general formula (III)

in which
   $R^1$ and $R^2$ have the abovementioned meaning,
in the presence of hydrogen and in the presence of a catalyst at temperatures between 0° C. and 200° C., if appropriate at elevated pressure.

Specifically, N-alkyl-arylamines of the formula

in which
   Ar represents a phenyl radical which is monosubstituted to trisubstituted by at least one of halogen, $C_1$–$C_4$-alkyl, $C_1$–$C_2$-halogenoalkyl, $C_1$–$C_4$-alkoxy, $C_1$–$C_2$-halogenoalkoxy or $C_1$–$C_4$-alkoxy-carbonyl,
   $R^1$ represents hydrogen or $C_1$–$C_4$-alkyl, and
   $R^2$ represents $C_1$–$C_6$-alkyl which is optionally substituted by halogen, or represents phenyl which is optionally substituted by at least one of halogen, $C_1$–$C_4$-alkyl or $C_1$–$C_4$-alkoxy, or, together with $R^1$, represents $C_2$–$C_6$-alkanediyl,
may be prepared in a one pot process by reacting a nitroarene of the formula

with a carbonyl compound of the formula

in the presence of hydrogen and in the presence of a palladium- or platinum-containing catalyst at a temperature between 0° C. and 200° C., the carbonyl compound being employed in excess and constituting the sole diluent for the reaction, the N-alkyl-arylamine being produced in a yield of at least 90% of theory, based upon 100% conversion.

More preferably, this process may be used to prepare a N-alkyl-arylamine of the formula

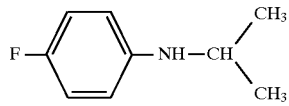

Additionally, this invention relates to a one-pot reaction of a nitroarene with a carbonyl compound in the presence of hydrogen and a Raney nickel, palladium or platinum catalyst to produce an N-alkyl-arylamine, the improvement which consists of employing as the nitroarene a compound of the formula

and a carbonyl compound of the formula

to produce an arylamine of the formula

wherein Ar, $R^1$ and $R^2$ are defined above.

Particularly preferred is this process wherein Ar is monofluorophenyl or difluorophenyl 2-fluoro-5-methylphenyl and the catalyst is selected from the group consisting of palladium metal, palladium(II) acetate, palladium(II) chloride, palladium(II) nitrate, palladium(II) oxide, platinum metal, platinum(II) chloride, platinum(IV) chloride or platinum (IV) oxide, chloride, platinum (IV) oxide and hydrates of the platinum salts.

Surprisingly, the N-alkyl-arylamines of the formula (I) can be obtained in virtually the theoretical yield in the process according to the invention, even though, in this case, several reaction stages are undergone in a so-called one-pot process and the stages give lower yields if carried out individually. Surprisingly, a competing reduction which is to be expected, of the carbonyl compounds employed as starting substances, is not observed to a noticeable extent.

Since the process according to the invention is carried out as a "one-pot process" and since, if appropriate, it can also be carried out without separate diluents, it compares particularly favorably with the known preparation methods of N-alkyl-arylamines.

If, for example, 4-fluoro-nitrobenzene and acetone are used as starting substances, the course of the reaction can be outlined by the following equation:

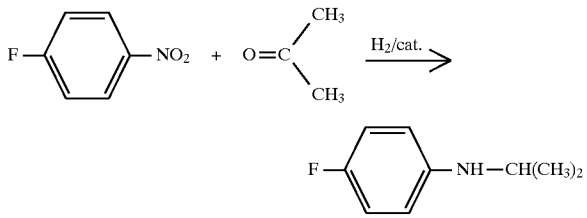

Formula (II) provides a general definition of the nitroarenes to be used as starting substances. In formula (II), Ar preferably represents a phenyl radical which is monosubstituted to trisubstituted by halogen, $C_1$–$C_4$-alkyl, $C_1$–$C_2$-halogenoalkyl, $C_1$–$C_4$-alkoxy, $C_1$–$C_2$-halogenoalkoxy and/or $C_1$–$C_4$-alkoxy-carbonyl.

Starting substances which are particularly preferred are the compounds of the formula (II) in which Ar represents a phenyl radical which is monosubstituted or disubstituted by fluorine, chlorine, bromine, methyl, ethyl, propyl, isopropyl, trifluoromethyl, methoxy, ethoxy, difluoromethoxy, trifluoromethoxy, 1,1,2,2-tetrafluoroethoxy, methoxycarbonyl, ethoxycarbonyl, propoxycarbonyl and/or isopropoxycarbonyl.

Examples of the starting substances of the formula (II) which may be mentioned are: 2-fluoro-, 3-fluoro-, 4-fluoro-, 2,3-difluoro-, 2,4-difluoro-, 2,5-difluoro-, 2,6-difluoro-, 3,4-difluoro- and 3,5-difluoro-nitrobenzene, 2-chloro-, 3-chloro-, 4,-chloro-, 2,3-dichloro-, 2,4-dichloro-, 2,5-dichloro-, 2,6-dichloro-, 3,4-dichloro- and 3,5-dichloro-nitrobenzene, 2-bromo-, 3-bromo- and 4-bromo-nitrobenzene, 2-methyl-, 3-methyl-, 4-methyl-, 2,3-dimethyl-, 2,4-dimethyl-, 2,5-dimethyl-, 2,6-dimethyl-, 3,4-dimethyl- and 3,5-dimethyl-nitrobenzene, 4-ethyl-, 4-propyl- and 4-isopropyl-nitrobenzene, 2-trifluoromethyl-, 3-trifluoromethyl-, 4-trifluoromethyl- and bis-(3,5-trifluoromethyl)-nitrobenzene, 2-methoxy-, 3--methoxy-, 4-methoxy- and bis-(3,5-methoxy)-nitrobenzene, 4-ethoxy-nitrobenzene, 2-difluoromethoxy-, 3-difluoromethoxy-and 4-difluoromethoxy-nitrobenzene, 2-trifluoromethoxy-, 3-trifluoromethoxy- and 4-trifluoromethoxy-nitrobenzene, 4-(1,1,2,2-tetrafluoroethoxy)-nitrobenzene, 4-methoxycarbonyl-, 4-ethoxycarbonyl-, 4-propoxycarbonyl- and 4-isopropoxycarbonyl-nitrobenzene.

The starting substances of the formula (II) are known and/or can be prepared by processes known per se (cf., for example, J. Am. Chem. Soc. 72 (1950), 2296–2297).

Formula (III) provides a general definition of the carbonyl compounds furthermore to be used as starting substances. In formula (III), $R^1$ preferably represents hydrogen or $C_1$–$C_4$-alkyl and $R^2$ preferably represents $C_1$–$C_6$-alkyl which is optionally substituted by halogen, or preferably represents phenyl which is optionally substituted by halogen, $C_1$–$C_4$-alkyl and/or $C_1$–$C_4$-alkoxy, or, together with $R^1$, preferably represents $C_2$–$C_6$-alkanediyl.

Particularly preferred starting substances are the compounds of the formula (III) in which $R^1$ represents hydrogen, methyl, ethyl, propyl, isopropyl, butyl or isobutyl and $R^2$ represents methyl, ethyl, propyl, isopropyl, butyl, isobutyl, sec-butyl, tert-butyl or phenyl, or, together with $R^1$, represents ethane-1,2-diyl ("dimethylene"), propane-1,3-diyl ("trimethylene"), butane-1,4-diyl ("tetramethylene") or pentane-1,5-diyl ("pentamethylene").

Examples of the starting substances of the formula (III) which may be mentioned are: acetaldehyde, propionaldehyde, butaldehyde, isobutaldehyde, benzaldehyde, acetone, methyl ethyl ketone, methyl propyl ketone, methyl isopropyl ketone, methyl butyl ketone, methyl isobutyl ketone, methyl-sec-butyl ketone, methyl tert-butyl ketone, diethyl ketone, dipropyl ketone, diisopropyl ketone, diisobutyl ketone, acetophenone, cyclopropanone, cyclobutanone, cyclopentanone and cyclohexanone.

The starting substances of the formula (III) are known chemicals for organic synthesis.

The process according to the invention is carried out in the presence of hydrogen and in the presence of a catalyst. Catalysts which are preferably suitable in this context are metals which are generally used as catalysts in catalytic hydrogenations, and also the salts of these metals.

Examples of the catalysts to be used according to the invention are: nickel, in particular Raney nickel, nickel(II) acetate, nickel(II) bromide, nickel(II) chloride, nickel(II) nitrate, nickel(II) sulphate, cobalt, cobalt(II) acetate, cobalt (II) chloride, cobalt(II) nitrate, cobalt(II) sulphate, copper, copper(II) acetate, copper(II) bromide, copper(II) chloride, copper(II) nitrate, copper(II) oxide, copper(II) sulphate, copper chromite, palladium, palladium(II) acetate, palladium(II) chloride, palladium(II) nitrate, palladium(II) oxide, platinum, platinum(II) chloride, platinum(IV) chloride and platinum(IV) oxide, the metal salts being employed as hydrates, if appropriate. Preferred catalyst metals are palladium and platinum.

It is preferred to employ the catalysts in finely divided form on suitable support materials such as, for example, active carbon or kieselguhr. Examples of particularly suitable catalyst/support combinations which may be mentioned are palladium or platinum on active carbon.

The process according to the invention can be carried out in the presence of diluents. Suitable diluents are aliphatic and aromatic hydrocarbons such as, for example, benzine, benzene and toluene, aliphatic alcohols such as, for example, methanol, ethanol, propanol and isopropanol, furthermore ethers such as, for example, diethyl ether, diisopropyl ether, methyl tert.-butyl ether and methyl tert.-amyl ether, tetrahydrofuran and dioxane.

When carrying out the process according to the invention, the reaction temperatures can be varied within a substantial range. In general, the process is carried out at temperatures between 0° C. and 200° C., preferably between 20° C. and 160° C., in particular between 30° C. and 120° C.

The process according to the invention is generally carried out in a pressure range between 1 and 200 bar, preferably between 5 and 150 bar, in particular between 10 and 120 bar.

For carrying out the process according to the invention, between 1 and 15 moles, in particular between 1 and 10 moles, of carbonyl compound of the formula (III) are generally employed per mole of nitroarene of the formula (II).

The starting substances of the formulae (II) and (III) are mixed, if appropriate in a diluent and preferably in an autoclave, and, after a catalyst has been added, the mixture is hydrogenated until the hydrogen uptake has come to an end. The catalyst is removed by filtration or centrifugation. The solution which remains is worked up by distillation, preferably under reduced pressure.

The N-alkyl-arylamines of the formula (I) which are to be prepared by the process according to the invention can be used as intermediates for agriculturally utilizable substances (cf. U.S. Pat. No. 4,418,021, DE-OS (German Published Specification) 3,821,600).

In the following examples, the retention index RI (OV 101) which is determined by gas chromatography is indicated to characterize the products obtained, the term "OV 101" denoting the column material used, namely dimethyl silicone manufactured by "Chrompack" under the name "DB1".

For the exact definition of the retention-index, cf. Milton L. Lee, Frank J. Yang and Keith D. Bartle, "Open Tubular Column Gas Chromatography, Theory and Practice, John Wiley & Sons, New York (1984), p. 216 et seq.

PREPARATION EXAMPLES

Example 1

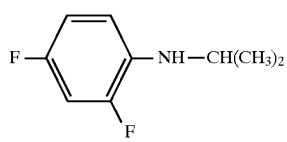

A mixture of 10.0 g (63 mmol) of 2,4-difluoro-nitrobenzene, 50 ml of acetone and 0.5 g of palladium/charcoal catalyst (containing 5% Pd) is hydrogenated at 60° C. and 100 bar hydrogen pressure. When the hydrogen uptake has come to an end, the catalyst is separated off by filtration with suction, and the solvent is carefully removed from the filtrate by distillation under a water pump vacuum at 30° C.

This gives 10.0 g (90.7% of theory) of 2,4-difluoro-N-isopropyl-aniline as an amorphous residue of a content, determined by gas chromatography, of 97.7%; retention index RI (OV 101): 1092.

Example 2

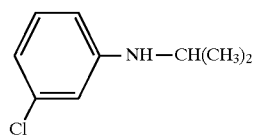

A mixture of 15.8 g (0.1 mol) of 3-chloronitro-benzene, 50 ml of methanol, 8.5 ml of acetone and 0.3 g of platinum/charcoal catalyst (5% Pt) is hydrogenated at 60° C. and 50 bar hydrogen pressure. When the hydrogen uptake has come to an end, the catalyst is separated off by filtration with suction, and the filtrate is carefully removed from the solvent by distillation under a water pump vacuum at 30° C.

This gives 16.1 g (95 % of theory) of 3-chloro-N-isopropyl-aniline as a liquid of a content, determined by gas chromatography, of 92.5%; retention index RI (OV 101): 1336.

The compounds of the formula (I)

listed in Table 1 below can, for example, also be prepared analogously to Example 1, 2 or 3a. Example 3a represents the best mode of preparing the instant compounds for large scale industrial production

Example 3a

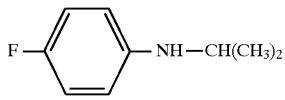

A mixture of 153 g (1.08 mol) of 4-fluoro-nitrobenzene, 500 ml of acetone and 9 g of platinum/charcoal catalyst (containing 5% Pt) is hydrogenated at 100° C. and 30 bar hydrogen pressure. When the hydrogen uptake has come to an end, the catalyst isseparated off by filtration with suction, and the excess of aceton is carefully removed from the filtrate by destillation under a water pump vacuum at 30° C.

This gives 163 g of 4-fluoro-N-isopropyl-aniline of a content, determined by gas chromatography, of 96.2% (corresponding to a yield of 94.4% of theory); rentention index Rl (OV 101):1146.

TABLE 1

| Example no. | Ar | $R^1$ | $R^2$ | Yield (% of theory) | RI (OV 101) |
|---|---|---|---|---|---|
| 3 | F—⟨⟩— | $CH_3$ | $CH_3$ | 90, 5 | 1146 |
| 4 | ⟨⟩— (F meta) | $CH_3$ | $CH_3$ | 92 | 1155 |
| 5 | ⟨⟩— ($F_3C$ meta) | $CH_3$ | $CH_3$ | 94 | 1167 |

TABLE 1-continued

| Example no. | Ar | R¹ | R² | Yield (% of theory) | RI (OV 101) |
|---|---|---|---|---|---|
| 6 | 4-fluoro-3-methyl (H₃C, F on phenyl) | CH₃ | CH₃ | 94 | 1171 |
| 7 | 3-chlorophenyl (Cl) | CH₃ | C₂H₅ | | |
| 8 | 4-fluorophenyl (F) | CH₃ | CH₂CH(CH₃)₂ | 93 | 1385 |
| 9 | 4-methylphenyl (H₃C) | CH₃ | CH₃ | 93 | 1227 |
| 10 | 3-methylphenyl (H₃C) | CH₃ | CH₃ | | |
| 11 | 3-methoxyphenyl (H₃CO) | CH₃ | CH₃ | | |
| 12 | 4-methoxyphenyl (H₃CO) | CH₃ | CH₃ | | |
| 13 | 3-trifluoromethoxyphenyl (F₃CO) | CH₃ | CH₃ | | |
| 14 | 4-difluoromethoxyphenyl (F₂CHO) | CH₃ | CH₃ | | |
| 15 | 3-difluoromethoxyphenyl (F₂HCO) | CH₃ | CH₃ | | |
| 16 | 4-fluorophenyl (F) | —CH₂CH₂CH₂CH₂— | | | |
| 17 | 4-fluorophenyl (F) | H | C₃H₇ | | |

TABLE 1-continued

| Example no. | Ar | R¹ | R² | Yield (% of theory) | RI (OV 101) |
|---|---|---|---|---|---|
| 18 | 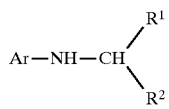 | —$CH_2CH_2CH_2CH_2CH_2$— | | 95 | 1549 |
| 19 |  | $C_3H_7$ | $CH_3$ | 95 | 1332 |
| 20 | 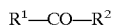 | $CH_3$ | $CH_3$ | | |
| 21 | 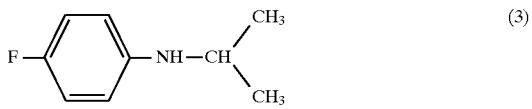 | $CH_3$ | $CH_3$ | | |

It will be understood that the specification and examples are illustrative but not limitative of the present invention and that other embodiments within the spirit and scope of the invention will suggest themselves to those skilled in the art.

We claim:

1. A one-pot process for the preparation of an N-alkyl-arylamine of the formula $$Ar-NH-CH\begin{matrix}R^1\\R^2\end{matrix} \quad (I)$$

in which

Ar represents a phenyl radical which is monosubstituted by fluorine or by trifluoromethyl or disubstituted by fluorine or by one fluorine and one methyl, $R^1$ represents hydrogen or $C_1$–$C_4$-alkyl, and $R^2$ represents $C_1$–$C_6$-alkyl or together with $R^1$, represents $C_2$–$C_6$-alkanediyl, consisting of reacting a nitroarene of the formula $$Ar-NO_2 \quad (II)$$

with a carbonyl compound of the formula $$R^1-CO-R^2 \quad (III)$$

in the presence of hydrogen and in the presence of a catalyst which consists essentially of (1) palladium metal, palladium (II) acetate, palladium (II) chloride, palladium (II) nitrate, palladium (II) oxide, platinum metal, platinum (11) chloride, platinum (IV) chloride, or platinum (IV) oxide or hydrates of the platinum salts; and (2) optionally a support, at a temperature between 0° C. and 200° C. and a pressure between 1 and 200 bar, wherein the carbonyl compound constitutes the sole diluent for the reaction, said carbonyl compound being employed in excess wherein up to 15 moles of the carbonyl compound are employed per mole of the nitroarene, the N-alkyl-arylamine being produced in a yield of at least 90% of theory.

2. A process according to claim 1, wherein Ar is 3-fluorophenyl, 4-fluorophenyl, 3-trifluoromethyl-phenyl, 2,4-difluorophenyl or 2-fluoro-5-methyl-phenyl.

3. A process according to claim 1, wherein the N-alkyl-arylamine (I) is of the formula

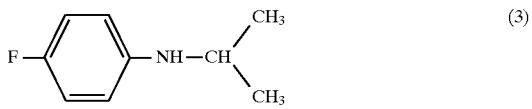
(3)

4-fluoro-nitrobenzene is employed as the nitroarene and acetone as the carbonyl compound, the reaction mixture consisting of the stated catalyst and the reactants, wherein the acetone is employed in excess and constitutes the sole diluent for the reaction, the 4-fluoro-N-isopropyl-aniline of the above formula (3) being produced in a yield of at least 90% of theory.

4. A process according to claim 1, wherein the catalyst is palladium or platinum on active carbon.

5. A process according to claim 1, carried out at a temperature between 20° and 160° C.

6. A process according to claim 1, carried out at a temperature between 30° C. and 120° C.

7. A process according to claim 15, carried out in a pressure range of 5 to,150 bar.

8. A process according to claim 1, carried out in a pressure range of 10 to 120 bar.

9. A process according to claim 1, wherein up to 10 moles of carbonyl compound (III) are employed per mole of nitroarene (II).

* * * * *

UNITED STATES PATENT AND TRADEMARK OFFICE
CERTIFICATE OF CORRECTION

PATENT NO : 5,817,876
DATED : October 6, 1998
INVENTOR(S): Fritz Maurer, et al.

It is certified that error appears in the above-identified patent and that said Letters Patent is hereby corrected as shown below:

Col. 10, Line 53        Delete claim "15" and substitute --1--

Signed and Sealed this

Second Day of November, 1999

Q. TODD DICKINSON

*Attest:*

*Attesting Officer*       *Acting Commissioner of Patents and Trademarks*